United States Patent [19]

Wentland et al.

[11] 4,032,529

[45] June 28, 1977

[54] AMINOMETHANOBENZAZOCINE INTERMEDIATES

[75] Inventors: Mark P. Wentland, North Greenbush; Noel F. Albertson, Schodack, both of N.Y.

[73] Assignee: Sterling Drug Inc., New York, N.Y.

[22] Filed: Nov. 24, 1975

[21] Appl. No.: 634,355

Related U.S. Application Data

[62] Division of Ser. No. 507,965, Sept. 20, 1974, Pat. No. 3,957,973.

[52] U.S. Cl. .......................... 260/293.54; 424/267
[51] Int. Cl.[2] ...................................... C07D 221/26
[58] Field of Search ............... 260/293.54, DIG. 13

[56] References Cited

UNITED STATES PATENTS 3,853,889  12/1974  Monkovic et al. ........... 260/293.55

*Primary Examiner*—Cecilia M. S. Jaisle
*Attorney, Agent, or Firm*—Theodore C. Miller; B. Woodrow Wyatt

[57] ABSTRACT

N-Alkylated-8-aminated-2,6-methano-3-benzazocines, useful as strong analgesics, are prepared by one route comprising reduction of 8-nitro intermediates or by another route comprising Birch type reduction of 8-methoxy intermediates followed by dehydration-rearrangement of the oximes of the resulting 8-oxo intermediates.

21 Claims, No Drawings

AMINOMETHANOBENZAZOCINE INTERMEDIATES

CROSS-REFERENCE TO RELATED APPLICATION

This application is a division of our copending application Ser. No. 507,965, filed Sept. 20, 1974 now U.S. Pat. No. 3,957,973.

SUMMARY OF THE INVENTION

This invention relates to intermediates and processes useful in the preparation N-alkylated-8-aminated-2,6-methano-3-benzazocines, which are useful as strong analgesics and which are more particularly defined as 1,2,3,4,5,6-hexahydro-3-Q-8-RR′N-5-X-6-Y-11-Z-11-Z′-2,6-methano-3-benzazocines having the formula Formula I wherein:
Q is propyl, isobutyl, neopentyl, allyl, 2-methyl-2-propenyl, 2-chloro-2-propenyl, cis-3-chloro-2-propenyl, cis-3-chloro-2-butenyl, trans-3-chloro-2-butenyl, propargyl, cyclopropylmethyl or (2,2-dichlorocyclopropyl)methyl;
R is hydrogen or methyl;
R′ is hydrogen, methyl, ethyl, propyl, isopropyl, butyl, isobutyl, sec-butyl, benzyl or cyclopropylmethyl;
X is hydrogen, methyl or ethyl;
Y is hydrogen, methyl, ethyl, propyl, allyl or phenyl;
Z is hydrogen, methyl, ethyl or hydroxy; and
Z′ is hydrogen, methyl or ethyl;
and acid addition salts thereof.

In addition to being useful as strong analgesics some of the compounds of Formula I are also useful as intermediates for preparing other compounds of Formula I and are thus one related intermediate aspect of the invention.

Another related intermediate aspect of the invention sought to be patented is 1,2,3,4,5,6-hexahydro-3-Q′-8-nitro-5-X-6-Y-11-Z-11-Z′-2,6-methano-3-benzazocine having the formula Formula II wherein:
Q′ is hydrogen, benzyl, propyl, isobutyl, neopentyl, allyl, 2-methyl-2-propenyl, 2-chloro-2-propenyl, cis-3-chloro-2-propenyl, cis-3-chloro-2-butenyl, trans-3-chloro-2-butenyl, propargyl, cyclopropylmethyl or (2,2-dichlorocyclopropyl)methyl;
X is hydrogen, methyl or ethyl;
Y is hydrogen, methyl, ethyl, propyl, allyl or phenyl;
Z is hydrogen, methyl, ethyl or hydroxy; and
Z′ is hydrogen, methyl or ethyl;
or an acid addition salt thereof.

Still another related intermediate aspect of the invention sought to be patented is 1,2,3,4,5,6,7,8,9,10-decahydro-3-Q′-8-oxo-5-X-6-Y-11-Z-11-Z′-2,6-methano-3-benzazocine having the formula Formula III wherein:
Q′ is hydrogen, benzyl, propyl, isobutyl, neopentyl, allyl, 2-methyl-2-propenyl, 2-chloro-2-propenyl, cis-3-chloro-2-propenyl, cis-3-chloro-2-butenyl, trans-3-chloro-2-butenyl, propargyl, cyclopropylmethyl or (2,2-dichlorocyclopropyl)methyl;
X is hydrogen, methyl or ethyl;
Y is hydrogen, methyl, ethyl, propyl, allyl or phenyl;
Z is hydrogen, methyl, ethyl or hydroxy; and
Z′ is hydrogen, methyl or ethyl;
or an acid addition salt thereof.

One related process aspect of the invention sought to be patented is the process which comprises reducing 1,2,3,4,5,6-hexahydro-3-Q′-8-nitro-5-X-6-Y-11-Z-11-Z′-2,6-methano-3-benzazocine of Formula II by a method effective in reducing 8-nitro to 8-amino without otherwise reducing or transforming the molecule to produce 1,2,3,4,5,6-hexahydro-3-Q′-8-amino-5-X-6-Y-11-Z-11-Z′-2,6-methano-3-benzazocine wherein:
Q′ is hydrogen, benzyl, propyl, isobutyl, neopentyl, allyl, 2-methyl-2-propenyl, 2-chloro-2-propenyl, cis-3-chloro-2-propenyl, cis-3-chloro-2-butenyl, trans-3-chloro-2-butenyl, propargyl, cyclopropylmethyl or (2,2-dichlorocyclopropyl)methyl;
X is hydrogen, methyl or ethyl;
Y is hydrogen, methyl, ethyl, propyl, allyl or phenyl;
Z is hydrogen, methyl, ethyl or hydroxy; and
Z′ is hydrogen, methyl or ethyl.

Another related process aspect of the invention sought to be patented is the process which comprises nitrating 1,2,3,4,5,6-hexahydro-3-Q′-5-X-6-Y-11-Z-11-Z′-2,6-methano-3-benzazocine to produce 1,2,3,4,5,6-hexahydro-3-Q′-8-nitro-5-X-6-Y-11-Z-11-Z′-2,6-methano-3-benzazocine of Formula II wherein:
Q′ is hydrogen, benzyl, propyl, isobutyl, neopentyl, allyl, 2-methyl-2-propenyl, 2-chloro-2-propenyl, cis-3-chloro-2-propenyl, cis-3-chloro-2-butenyl, trans-3-chloro-2-butenyl, propargyl, cyclopropylmethyl of (2,2-dichlorocyclopropyl)methyl;
X is hydrogen, methyl or ethyl;
Y is hydrogen, methyl, ethyl, propyl, allyl or phenyl;
Z is hydrogen, methyl, ethyl or hydroxy; and
Z′ is hydrogen, methyl or ethyl.

Still another related process aspect of the invention sought to be patented is the process which comprises reducing 1,2,3,4,5,6-hexahydro-3-Q′-8-methoxy-5-X-6-Y-11-Z-11-Z′-2,6-methano-3-benzazocine by a reduction of the Birch type to produce 1,2,3,4,5,6,7,8,9,10-decahydro-3-Q′-8-oxo-5-X-6-Y-11-Z-11-Z′-2,6-methano-3-benzazocine of Formula III wherein:

Q' is hydrogen, benzyl, propyl, isobutyl, neopentyl, allyl, 2-methyl-2-propenyl, 2-chloro-2-propenyl, cis-3-chloro-2-propenyl, cis-3-chloro-2-butenyl, trans-3-chloro-2-butenyl, propargyl, cyclopropylmethyl or (2,2-dichlorocyclopropyl)methyl;

X is hydrogen, methyl or ethyl;
Y is hydrogen, methyl, ethyl, propyl, allyl or phenyl;
Z is hydrogen, methyl, ethyl or hydroxy; and
Z' is hydrogen, methyl or ethyl.

One intermediate aspect of the invention sought to be patented is 1,2,3,4,5,6,7,8,9,10-decahydro-3-Q'-8-hydroxyimino-5-X-6-Y-11-Z-11-Z'-2,6-methano-3-benzazocine having the formula

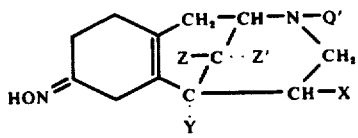

Formula IV wherein:
Q' is hydrogen, benzyl, propyl, isobutyl, neopentyl, allyl, 2-methyl-2-propenyl, 2-chloro-2-propenyl, cis(-3-chloro-2-propenyl, cis-3-chloro-2-butenyl, trans-3-chloro-2-butenyl, propargyl, cyclopropylmethyl or (2,2-dichlorocyclopropyl)methyl;
X is hydrogen, methyl or ethyl;
Y is hydrogen, methyl, ethyl, propyl, allyl or phenyl;
Z is hydrogen, methyl, ethyl or hydroxy; and
Z' is hydrogen, methyl or ethyl;
or an acid addition salt thereof.

Another intermediate aspect of the invention sought to be patented is 1,2,3,4,5,6-hexahydro-3-Q°-8-RR'N-5-X-6-Y-11-Z-11-Z'-2,6-methano-3-benzazocine having the formula

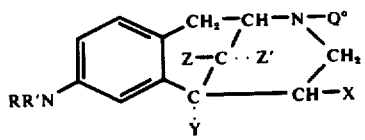

Formula V wherein:
Q° is hydrogen or benzyl;
R is hydrogen or methyl;
R' is hydrogen, methyl, ethyl, propyl, isopropyl, butyl, isobutyl, sec-butyl, benzyl or cyclopropylmethyl;
X is hydrogen, methyl or ethyl;
Y is hydrogen, methyl, ethyl, propyl, allyl or phenyl;
Z is hydrogen, methyl, ethyl or hydroxy; and
Z' is hydrogen, methyl or ethyl;
or an acid addition salt thereof.

Still another intermediate aspect of the invention sought to be patented is 1,2,3,4,5,6-hexahydro-3-Q"-8-RR'N-5-X-6-Y-11-Z-11-Z'-2,6-methano-3-benzazocine having the formula

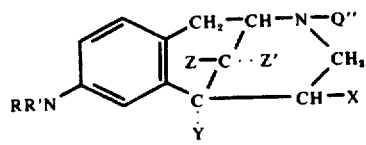

Formula VI wherein:
Q" is formyl, acetyl or Q* wherein Q* is propionyl, isobutyryl, pivaloyl, acryloyl, 2-methylacryloyl, 2-chloroacryloyl, cis-3-chloroacryloyl, cis-3-chlorocrotonyl, trans-3-chlorocrotonoyl, propiolyl, cyclopropanecarbonyl or 2,2-dichlorocyclopropanecarbonyl;
R is hydrogen or methyl;
R' is hydrogen, methyl, ethyl, propyl, isopropyl, butyl, isobutyl, sec-butyl, benzyl or cyclopropylmethyl;
X is hydrogen, methyl or ethyl;
Y is hydrogen, methyl, ethyl, propyl, allyl or phenyl;
Z is hydrogen, methyl, ethyl or hydroxy; and
Z' is hydrogen, methyl or ethyl;
or an acid addition salt thereof.

Yet another intermediate aspect of the invention sought to be patented is 1,2,3,4,5,6-hexahydro-3-Q"-8-nitro-5-X-6-11-Z-11-Z'-2,6-methano-3-benzazocine having the formula

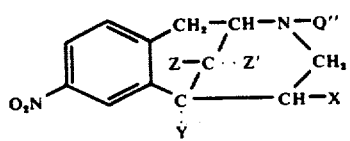

Formula VII wherein:
Q" is formyl, acetyl or Q* wherein Q* is propionyl, isobutyryl, pivaloyl, acryloyl, 2-methylacryloyl, 2-chloroacryloyl, cis-3-chloroacryloyl, cis-3-chlorocrotonoyl, trans-3-chlorocrotonoyl, propiolyl, cyclopropanecarbonyl or 2,2-dichlorocyclopropanecarbonyl;
X is hydrogen, methyl or ethyl;
Y is hydrogen, methyl, ethyl, propyl, allyl or phenyl;
Z is hydrogen, methyl, ethyl or hydroxy; and
Z' is hydrogen, methyl or ethyl.

Even another intermediate aspect of the invention sought to be patented is 1,2,3,4,5,6-hexahydro-3-Q'-8-RR"N-5-X-6-Y-11-Z-11-Z'-2,6-methano-3-benzazocine having the formula

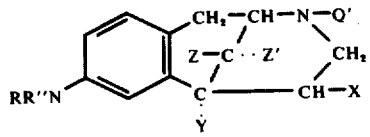

Formula VIII wherein:
Q' is hydrogen, benzyl, propyl, isobutyl, neopentyl, allyl, 2-methyl-2-propenyl, 2-chloro-2-propenyl, cis-3-chloro-2-propenyl, cis-3-chloro-2-butenyl, trans-3-chloro-2-butenyl, propargyl, cyclopropylmethyl or (2,2-dichlorocyclopropyl)methyl;
R is a hydrogen or methyl;
R" is formyl, acetyl, propionyl, butyryl, isobutyryl, benzoyl or cyclopropanecarbonyl;
X is hydrogen, methyl or ethyl;

is hydrogen, methyl, ethyl, propyl, allyl or phenyl;
Z is hydrogen, methyl, ethyl or hydroxy; and
Z' is hydrogen, methyl or ethyl;
or an acid addition salt thereof.

Finally another intermediate aspect of the invention sought to be patented is 1,2,3,4,5,6-hexahydro-3-Q"-8-RR"N-5-X-6-Y-11-Z-11-Z'-2,6-methano-3-benzazocine having the formula

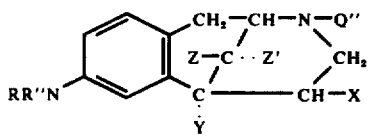

Formula IX wherein:
Q" is formyl, acetyl or Q* wherein Q* is propionyl, isobutyryl, pivaloyl, acryloyl, 2-methylacryloyl, 2-chloroacryloyl, cis-3-chloroacryloyl, cis-3-chlorocrotonoyl, trans-3-chlorocrotonoyl, propiolyl, cyclopropanecarbonyl or 2,2-dichlorocyclopropanecarbonyl;
R is hydrogen or methyl;
R" is formyl, acetyl, propionyl, butyryl, isobutyryl, benzoyl or cyclopropanecarbonyl;
X is hydrogen, methyl or ethyl;
Y is hydrogen, methyl, ethyl, propyl, allyl or phenyl;
Z is hydrogen, methyl, ethyl or hydroxy; and
Z' is hydrogen, methyl or ethyl.

The compounds of Formulas II–IX are useful as intermediates for preparing compounds of Formula I.

A process aspect of the invention sought to be patented is the process which comprises dehydrating and rearranging 1,2,3,4,5,6,7,8,9,10-decahydro-3-Q'-8-hydroxyimino-5-X-6-Y-11-Z-11-Z'-2,6-methano-3-benzazocine of Formula IV to produce 1,2,3,4,5,6-hexahydro-3-Q'-8-amino-5-X-6-Y-11-Z-11-Z'-2,6-methano-3-benzazocine wherein:
Q' is hydrogen, benzyl, propyl, isobutyl, neopentyl, allyl, 2-methyl-2-propenyl, 2-chloro-2-propenyl, cis-3-chloro-2-propenyl, cis-3-chloro-2-butenyl, trans-3-chloro-2-butenyl, propargyl, cyclopropylmethyl or (2,2-dichlorocyclopropyl)methyl;
X is hydrogen, methyl or ethyl;
Y is hydrogen, methyl, ethyl, propyl, allyl or phenyl;
Z is hydrogen, methyl, ethyl or hydroxy; and
Z' is hydrogen, methyl or ethyl.

Another process aspect of the invention sought to be patented is the process which comprises selectively hydrolyzing 1,2,3,4,5,6-hexahydro-3-Q"-8-RR"N-5-X-6-Y-11-Z-11-Z'-2,6-methano-3-benzazocine of Formula IX by a method effective in removing R" without removing Q" to produce 1,2,3,4,5,6-hexahydro-3-Q"-8-RHN-5-X-6-Y-11-Z-11-Z'-2,6-methano-3-benzazocine wherein:
Q" is formyl, acetyl or Q* wherein Q* is propionyl, isobutyryl, pivaloyl, acryloyl, 2-methylacryloyl, 2-chloroacryloyl, cis-3-chloroacryloyl, cis-3-chlorocrotonoyl, trans-3-chlorocrotonoyl, propiolyl, cyclopropanecarbonyl or 2,2-dichlorocyclopropanecarbonyl;
R is hydrogen or methyl;
R" is formyl, acetyl, propionyl, butyryl, isobutyryl, benzoyl or cyclopropanecarbonyl;
X is hydrogen, methyl or ethyl;
Y is hydrogen, methyl, ethyl, propyl, allyl or phenyl;
Z is hydrogen, methyl, ethyl or hydroxy; and
Z' is hydrogen, methyl or ethyl.

Still another process aspect of the invention sought to be patented is the process which comprises reducing 1,2,3,4,5,6-hexahydro-3-Q"-8-nitro-5-X-6-Y-11-Z'-2,6-methano-3-benzazocine of Formula VII by a method effective in reducing 8-nitro to 8-amino without otherwise reducing or transforming the molecule to produce 1,2,3,4,5,6-hexahydro-3-Q'-8-amino-5-X-6-Y-11-Z-11-Z'-2,6-methano-3-benzazocine wherein:
Q" is formyl, acetyl or Q* wherein Q* is propionyl, isobutyryl, pivaloyl, acryloyl, 2-methylacryloyl, 2-chloroacryloyl, cis-3-chloroacryloyl, cis-3-chlorocrotonoyl, trans-3-chlorocrotonoyl, propiolyl, cyclopropanecarbonyl or 2,2-dichlorocyclopropanecarbonyl;
X is hydrogen, methyl or ethyl;
Y is hydrogen, methyl, ethyl, propyl, allyl or phenyl;
Z is hydrogen, methyl, ethyl or hydroxy; and
Z' is hydrogen, methyl or ethyl.

Yet another process aspect of the invention sought to be patented is the process which comprises reducing 1,2,3,4,5,6-hexahydro-3-Q*-8-RR'N-5-X-6-Y-11-Z-11-Z'-2,6-methano-3benzazocine of Formula VI by a method effective in reducing 3Q* to 3Q without otherwise reducing or transforming the molecule to produce 1,2,3,4,5,6-hexahydro-3-Q-8-RR'-N-5-X-6-Y-11-Z-11-Z'-2,6-methano-3-benzazocine of Formula I wherein:
Q is propyl, isobutyl, neopentyl, allyl, 2-methyl-2-propenyl, 2-chloro-2-propenyl, cis-3-chloro-2-propenyl, cis3-chloro-2-butenyl, trans-3-chloro-2-butenyl, propargyl, cyclopropylmethyl or (2,2,-dichlorocyclopropyl)methyl; *L6 Q* is propionyl, isobutyryl, pivaloyl, acryloyl, 2-methylacryloyl, 2-chloroacryloyl, cis-3-chloroacryloyl, cis-3-chlorocrotonoyl, trans-3-chlorocrotonoyl, propiolyl, cyclopropanecarbonyl or 2,2-dichlorocyclopropanecarbonyl;
R is hydrogen or methyl;
R' is hydrogen, methyl, ethyl, propyl, isopropyl, butyl, isobutyl, sec-butyl, benzyl or cyclopropylmethyl;
X is hydrogen, methyl or ethyl;
Y is hydrogen, methyl, ethyl, propyl, allyl or phenyl;
Z is hydrogen, methyl, ethyl or hydroxy; and
Z' is hydrogen, methyl or ethyl.

DETAILED DESCRIPTION OF THE INVENTION

The compounds of Formulas I–IX can each exist as one or the other optical isomer or a mixture thereof. The features $$\overset{C}{\underset{Y}{|}}$$

and C..Z' represent bonds oriented below the plane of the page if the plane of the tetralin moiety is considered to be in the plane of the page. When Z is methyl, ethyl or hydroxy, it is referred to as equatorial (eq) with respect to the tetralin moiety and trans with respect to Y. When Z is hydroxy, the 11-carbon atom is SR in chirality and the compound is in the α-series of benzomorphans as designated by May and coworkers (see Nathan B. Eddy and Everette L. May, Synthetic Analgesics, Part IIB of Parts IIA and IIB, Pergamon Press, Oxford, 1966, pp. 117–137). When Z' is methyl or ethyl, it is referred to as axial (ax) with respect to the tetralin moiety and cis with respect to Y. When X is methyl or ethyl, it is referred to as equatorial with respect to the hexahydrobenzazocine moiety and trans with respect to Y.

The compounds of Formulas I–VI and VIII are amino bases and react with organic and inorganic acids to form acid addition salts. Due to the presence of the basic amino grouping, the free base forms represented by the formulas react with organic and inorganic acids to form acid addition salts. The acid addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid addition salt is isolated by filtration, if it is insoluble in the reaction medium, or by evaporation of the reaction medium to leave the acid addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acidm sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid, and the like. All of the acid addition salts are useful as sources of the free bases by reaction with a stronger base. Thus, if one or more characteristics such as solubility, molecular weight, physical appearance, toxicity or the like or a given base or acid addition salt thereof render that form unsuitable for the purpose at hand, it can be readily converted to another, more suitable form. For pharmaceutical purposes, acid addition salts of relatively non-toxic, pharmaceutically-acceptable acids, for example hydrochloric acid, lactic acid, tartaric acid, and the like, are of course employed. Either the free bases or the acid addition salts thereof may crystallize as crystalline solvates with solvent of crystallization in integral or fractional amounts, for example, as the hydrate sesquihydrate or ethanolate.

The manner and process of making and using the invention and the best mode of carrying it out will now be described so as to enable any person skilled in the art to which it pertains to make and use it.

The process which comprises reducing 1,2,3,4,5,6-hexahydro-3-Q'-8-nitro-5-X-6-Y-11-Z-11-Z'-2,6-methano-3-benzazocine of Formula II is carried out by any method effective in reducing 8-nitro to 8-amino without otherwise reducing or transforming the molecule, for example, by the use of iron and aqueous hydrochloric acid. A cosolvent, for example, ethanol can be used. A buffering agent, for example, sodium acetate, can also be used. The rate of the reduction can be controlled by heating or cooling. The process which comprises reducing 1,2,3,4,5,6-hexahydro-3-Q''-8-nitro-5-X-6-Y-11-Z-11-Z'-2,6-methano-3-benzazocine of Formula VII is carried out similarly.

The process which comprises dehydrating and rearranging 1,2,3,4,5,6,7,8,9,10-decahydro-3-Q'-8-hydroxyimino-5-X-6-Y-11-Z-11-Z'-2,6-methano-3-benzazocine of Formula IV is effectively an aromatization process and is carried out by any method effective in dehydrating the oxime without otherwise dehydrating or transforming the molecule, for example, by the use of hydrochloric acid and acetic anhydride. A solvent, for example, acetic acid, can be used. The rate of the aromatization can be controlled by heating or cooling. The use of hydrochloric acid and acetic anhydride on the compounds of Formula IV produces the corresponding compounds of Formula VIII wherein R is hydrogen and R'' is acetyl and the corresponding compounds of Formula IX wherein R is hydrogen and Q'' and R'' are both acetyl, which can be isolated or can be hydrolyzed without isolation to remove acetyl.

The 8-nitro reductions and the 8-hydroxyimino dehydration-rearrangement-hydrolysis sequence are alternative processes and produce only the corresponding compounds of Formulas I, V and VI wherein R and R' are both hydrogen, which can be used as intermediates for preparing the remaining compounds of Formulas I, V and VI wherein R is methyl and R' is methyl, ethyl, propyl, isopropyl, butyl, isobutyl, sec-butyl, benzyl or cyclopropylmethyl, which are prepared either by alkylation or by an acylation-reduction sequence. The alkylation is accomplished using, for example, dimethyl sulfate, ethyl iodide, propyl bromide, isopropyl bromide, butyl methanesulfonate, isobutyl bromide, sec-butyl bromide, benzyl chloride or cyclopropylmethyl bromide. Dimethylation is preferably accomplished by catalytic hydrogenative methylation using formaldehyde and palladium-on-carbon as catalyst or, alternatively, by reductive methylation using formaldehyde and formic acid. Monobenzylation is preferably accomplished by reductive benzylation using benzaldehyde and sodium borohydride. The acylation step of the acylation reduction sequence affords the corresponding compounds of Formulas VIII and IX and is accomplished using, for example, formic-acetic anhydride, acetic anhydride, propionic anhydride, butyric anhydride, isobutyryl chloride, benzoyl chloride or cyclopropanecarbonyl chloride. The reduction step of the acylation-reduction sequence is accomplished using, for example, diborane or lithium aluminum hydride and results in the simultaneous reduction of Q* in the compounds of Formula IX to the corresponding Q in the compounds of Formula I.

A third alternative process for preparing the compounds of Formula I is the process which comprises reducing the corresponding 1,2,3,4,5,6-hexahydro-3-Q*-8-RR'N-5-X-6-Y-11-Z-11-Z'-2,6-methano-3-benzazocine of Formula VI, which is also accomplished using, for example, lithium aluminum hydride.

Producing the desired combination of Q, R and R' in the compounds of Formula I may require the use of protecting groups during N-alkylation or N-acylation. Benzyl is such a protecting group in the compounds of Formula VIII wherein Q' is benzyl and can be removed, for example, by catalytic hydrogenation using palladium as catalyst. Formyl and acetyl are such protecting groups in the compounds of Formula VI wherein Q" is formyl or acetyl and can be removed, for example, by hydrolysis.

In the compounds of Formula IX R" is selectively removed without removing Q" in the process which comprises selectively hydrolyzing 1,2,3,4,5,6-hexahydro-3-Q"-8-RR"N-5-X-6-Y-11-Z-11-Z'-2,6-methano-3-benzazocine of Formula IX, which is accomplished using, for example, dilute hydrochloric acid. The rate of the selective hydrolysis can be controlled by heating or cooling.

The process which comprises nitrating 1,2,3,4,5,6-hexahydro-3-Q'-5-X-6-Y-11-Z-11-Z'-2,6-methano-3-benzazocine to produce 1,2,3,4,5,6-hexahydro-3-Q'-8-nitro-5-X-6-Y-11-Z-11-Z'-2,6-methano-3-benzazocine of Formula II is carried out by any method effective in substituting nitro for hydrogen at the 8-position of the aromatic ring without otherwise transforming the molecule, for example, by the use of nitric acid. A solvent is preferably used, for example, acetic acid. The rate of the nitration can be controlled by heating or cooling. 1,2,3,4,5,6-Hexahydro-3-Q"-8-nitro-5-X-6-Y-11-Z-11-Z'-2,6-methano-3-benzazocine of Formula VII is similarly obtained by nitrating 1,2,3,4,5,6-hexahydro-3-Q"-5-X-6-Y-11-Z-11-Z'-2,6-methano-3-benzazocine.

The process which comprises reducing 1,2,3,4,5,6-hexahydro-3-Q'-8-methoxy-5-X-6-Y-11-Z-11-Z'-2,6-methano-3-benzazocine is carried out by a reduction of the Birch type (The Merck Index, Eighth Edition, Merck & Co., Rahway, N.J., 1968, p. 1146) using, for example, sodium and liquid ammonia. A cosolvent, for example, a mixture of tetrahydrofuran and isopropyl alcohol can be used. 1,2,3,4,5,6,7,10-Octahydro-3-Q'-8-methoxy-5-X-6-Y-11-Z-11-Z'-2,6-methano-3-benzazocine is the immediate product and is easily hydrolyzed using, for example, dilute hydrochloric acid to produce 1,2,3,4,5,6,7,8,9,10-decahydro-3-Q'-8-oxo-5-X-6-Y-11-Z-11-Z'-2,6-methano-3-benzazocine of Formula III. If Q' is benzylic or allylic, it is removed by the reduction, but can be replaced by one of the methods described below.

The compounds of Formula IV are prepared from the corresponding compounds of Formula III using hydroxylamine or an acid addition salt thereof, for example, hydroxylamine hydrochloride.

In the compounds of Formulas VI, VII and IX Q" is introduced by acylation of the corresponding compounds of Formula V wherein Q° is hydrogen, the compounds of Formula II wherein Q' is hydrogen and the compounds of Formula VIII wherein Q' is hydrogen, respectively, using, for example, formic-acetic anhydride, acetic anhydride, propionyl chloride, isobutyryl chloride, pivaloyl chloride, 2-methylacryloyl chloride, 2-chloroacryloyl chloride, cis-3-chloroacryloyl chloride, cis-3-chlorocrotonoyl chloride, trans-3-chlorocrotonoyl chloride, propiolyl chloride, cyclopropanecarbonyl chloride or 2,2-dichlorocyclopropanecarbonyl chloride. Alternatively, Q" is built into the compounds of Formula VII by first acylating the corresponding 1,2,3,4,5,6-hexahydro-5-X-6-Y-11-Z-11-Z'-2,6-methano-3-benzazocine and then nitrating the resulting 1,2,3,4,5,6-hexahydro-3-Q"-5-X-6-Y-11-Z-11-Z'-2,6-methano-3-benzazocine as described above.

Thus, Q can be built into the compounds of Formula I by an acylation-reduction sequence through the corresponding Q*, which appears in the compounds of Formulas VI, VII and IX, as described above, or, alternatively, by alkylation in the corresponding compounds of Formulas II, III and VIII wherein Q" is hydrogen, the corresponding 1,2,3,4,5,6-hexahydro-5-X-6-Y-11-Z-11-Z'-2,6-methano-3-benzazocines prior to 8-nitration or the corresponding 1,2,3,4,5,6-hexahydro-8-methoxy-5-X-6-Y-11-Z-11-Z'-2,6-methano-3-benzazocines prior to the Birch reduction using, for example, propyl bromide, isobutyl bromide, neopentyl bromide, allyl chloride, 2-methyl-2-propenyl chloride, 2-chloro-2-propenyl chloride, cis-3-chloro-2-propenyl chloride, cis-3-chloro-2-butenyl chloride, trans-3-chloro-2-butenyl chloride, propargyl bromide, cyclopropylmethyl bromide or (2,2-dichlorocyclopropyl)methyl bromide.

Some of the 1,2,3,4,5,6-hexahydro-3-Q'-5-X-6-Y-11-Z-11-Z'-2,6-methano-3-benzazocines, 1,2,3,4,5,6-hexahydro-3-Q'-methoxy-5-X-6-Y-11-Z-11-Z'-2,6-methano-3-benzazocines, 1,2,3,4,5,6-hexahydro-3-Q"-5-X-6-Y-11-Z-11-Z'-2,6-methano-3-benzazocines and 1,2,3,4,5,6-hexahydro-3-Q"-8-methoxy-5-X-6-Y-11-Z-11-Z'-2,6-methano-3-benzazocines are known; those which are not known are prepared from the corresponding 1,2,3,4,5,6-hexahydro-5-X-6-Y-11-Z-11-Z'-2,6-methano-3-benzazocines and 1,2,3,4,5,6-hexahydro-8-methoxy-5-X-6-Y-11-Z-11-Z'-2,6-methano-3-benzazocines by the methods described above. Some of the 1,2,3,4,5,6-hexahydro-5-X-6-Y-11-Z-11-Z'-2,6-methano-3-benzazocines and 1,2,3,4,5,6-hexahydro-8-methoxy-5-X-6-Y-11-Z--11-Z'-2,6-methoxy-3-benzazocines are known; those which are not known are preapred, for example, from the corresponding 1,2,3,4,5,6-hydrohydro-3-methyl-5-X-6-Y-11-Z-11-Z'-2,6-methano-3-benzazocines and 1,2,3,4,5,6-hexahydro-3-methyl-8-methoxy-5-X-6-Y-11-Z-11-Z'-2,6-methano-3-benzazocines, for example, by cyanogenation with cyanogen bromide followed by hydrolysis of the resulting 1,2,3,4,5,6-hexahydro-3-cyano-5-X-6-Y-11-Z-11-Z'-2,6-methano-3 -benzazocines and 1,2,3,4,5,6-hexahydro-3-cyano-8-methoxy-5-X-6-Y-11-Z-11-Z'-2,6-methano-3-benzazocines.

Those 1,2,3,4,5,6-hexahydro-3-methyl-8-methoxy-5-X-6-Y-11-Z-11-Z'-2,6-methano-3-benzazocines which are not known are prepared from the corresponding 1,2,3,4,5,6-hexahydro-3-methyl-8-hydroxy-5X-6-Y-11-Z-11-Z'-2,6-methano-3-benzazocines by O-methylation using, for example, diazomethane.

The various combinations of the X-, Y-, Z- and Z'-substituents in the 1,2,3,4,5,6-hexahydro-5-X-6-Y-11-Z-11-Z'-2,6-methano-3-benzazocines and 1,2,3,4,5,6-hexahydro-8-methoxy-5-X-6-Y-11-Z-11-Z'-2,6-methano-3-benzazocines are known or are prepared by known methods. See, for example, Eddy and May (reference cited above), Parfitt and Walters (J. Med. Chem., Vol. 14, No. 7, 1971, pp. 565–568), May and co-workers (J. Med. Chem., Vol. 12, No. 2, 1969, pp. 405–408), U.S. Pat. No. 3,320,265, British Pat. Nos. 1,299,699 and 1,299,700 and Netherlands Application No. 73/14758.

The following examples illustrate the invention. Structures of compounds are inferred from reaction types. Confirmations of structures are made by analyses of the elements, ultraviolet spectra, infrared spectra, nuclear magnetic resonance spectra and/or mass spectra. Courses of reactions and homogeneities of products are ascertained by thin layer chromatography and/or gas-liquid chromatography. Melting and boiling points or ranges are uncorrected unless otherwise indicated.

EXAMPLE 1

A. A solution of 3-(cyclopropylmethyl)-1,2,3,4,5,6-hexahydro-cis-6,11-dimethyl-2,6-methano-3-benzazocine (Example 1 of U.S. Pat. No. 3,382,249, 11.0 g.) in acetic acid (50 ml.) was added with stirring and cooling (at 2.5°–5° C.) to a solution of red fuming nitric acid (155 ml.) and acetic acid (90 ml.). The temperature was allowed to rise slowly to room temperature. After being allowed to stand overnight the solution was purged with a stream of air, then partially evaporated (at 55°–60° C.) under reduced pressure to a yellow liquid (148 g.), to which was added a solution of sodium hydroxide (85 g.) in water. A solution of the resulting product in chloroform was washed with water, dried and concentrated, affording a red syrup (11.6 g.). A solution of the red syrup in ether was filtered. Addition of ethereal hydrochloric acid to the filtrate and recrystallization of the product (10.3 g.) from ethanol afforded off-white crystals of 3-(cyclopropylmethyl)-1,2,3,4,5,6-hexahydro-cis-6,11-dimethyl-8-nitro-2,6-methano-3-benzazocine hydrochloride (7.2 g., m.p. 283°–284° C.). The free base was obtained as an orange syrup from the salt using sodium hydroxide and is the compound of Formula II wherein Q' is cyclopropylmethyl, X is hydrogen, Y is methyl, Z is hydrogen and Z' is methyl.

B. Iron powder (13.2 g.) was added portionwise to a solution of 3-(cyclopropylmethyl)-1,2,3,4,5,6-hexahydro-cis-6,11-dimethyl-8-nitro-2,6-methano-3-benzazocine (the free base product of part (A) of this example, 11.6 g.) water (35 ml.), ethanol (60 ml.) and concentrated hydrochloric acid (3.66 ml.) and the mixture was stirred under reflux. Sodium bicarbonate (5 g.) was added, the resulting mixture was filtered and the filtrate was concentrated under reduced pressure. Ether and ethanol were added to the residual yellow syrup, the resulting mixture was filtered and the filtrate was concentrated. Hydrogen chloride was added to a solution of part (5.47 g.) of the resulting red syrup (10.4 g.) in ethanol. Recrystallization of the product (m.r. 303°–306° C.) from methanol-ether afforded off-white crystals of 8-amino-3-(cyclopropylmethyl)-1,2,3,4,5,6-hexahydro-cis-6,11-dimethyl-2,6-methano-3-benzazocine dihydrochloride (2.71 g., m.p. 314°–316° C.), the free base of which is the compound of Formula I wherein Q is cyclopropylmethyl, R is hydrogen, R' is hydrogen, X is hydrogen, Y is methyl, Z is hydrogen and Z' is methyl.

C. A solution of the 1,2,3,4,5,6-hexahydro-cis-6,11-dimethyl-2,6-methano-3-benzazocine (the free base of which is the compound described as 5,9-dimethyl-6,7-benzomorphan picrate and hydrochloride at J. Org. Chem., 24, 117 (1959); 40.4 g.) in acetic acid (320 ml.) was added to a solution of nitric acid (90%, 600 ml.) and acetic acid (400 ml.) with cooling (to 5°±1° C.) and stirring. The resulting mixture was allowed to warm to room temperature, poured onto ice (4500 ml.), basified with sodium hydroxide solution (35%) and extracted with ether. The ether extracts were dried and concentrated, affording a syrup (40.0 g.). Hydrogen chloride was added to a solution of the syrup in acetone. Recrystallization of the product (27.5 g., m.p. 252°–255° C.) from ethanol afforded as a white powder 1,2,3,4,5,6-hexahydro-6(eq),11(ax)-dimethyl-8-nitro-2,6-methano-3-benzazocine hydrochloride (16.9 g., m.p. 266°–268° C.), the free base of which is the compound of Formula II wherein Q' is hydrogen, X is hydrogen, Y is methyl, Z is hydrogen and Z' is methyl.

D. Acylation of 1,2,3,4,5,6-hexahydro-6(eq),11(ax)-dimethyl-8-nitro-2,6-methano-3-benzazocine (the free base of the product of part (C) of this example) with cyclopropanecarbonyl chloride provides 1,2,3,4,5,6-hexahydro-3-cyclopropanecarbonyl-8-nitro-6(eq),1-1(ax)-dimethyl-2,6-methano-3-benzazocine, the compound of Formula VII wherein Q'' is cyclopropanecarbonyl, X is hydrogen, Y is methyl, Z is hydrogen and Z' is methyl.

E. Reduction of 1,2,3,4,5,6-hexahydro-3-cyclopropanecarbonyl-8-nitro-6(eq),11(ax)-dimethyl-2,6-methano-3-benzazocine (the product of part (D) of this example) using iron and hydrochloric acid provides 1,2,3,4,5,6-hexahydro-3-cyclopropanecarbonyl-8-amino-6(eq),11(ax)-dimethyl-2,6-methano-3-benzazocine, the compound of Formula VI wherein Q'' is cyclopropanecarbonyl, R is hydrogen, R' is hydrogen, X is hydrogen, Y is methyl, Z is hydrogen and Z' is methyl.

F. Reduction of 1,2,3,4,5,6-hexahydro-3-cyclopropanecarbonyl-8-amino-6(eq),11(ax)-dimethyl-2,6-methano-3-benzazocine (the product of part (E) of this example) using lithium aluminum hydride provides 8-amino-3-cyclopropylmethyl)-1,2,3,4,5,6-hexahydro-cis-6,11-dimethyl-2,6-methano-3-benzazocine, which is identical with the free base product of part B of this example.

G. A solution of 3-(cyclopropylmethyl)-1,2,3,4,5,6-hexahydro-8-methoxy-6-(eq),11(ax)-dimethyl-2,6-methano-3-benzazocine (the free base product of part (A) of Example 20 of U.S. Pat. No. 3,372,165, 50.0 g.), tetrahydrofuran (500 ml.) and isopropyl alcohol (500 ml.) was added with stirring to liquid ammonia (about 1.5 l.) under reflux. Sodium (69.5 g.) was then added in small (about 1 g.) pieces with continued stirring (during ½ hr.). After the blue color of the solution had disappeared (about 1 hr. more), methanol (200 ml.) was added, the condenser was removed and the ammonia was allowed to evaporate overnight. The residual cloudy solution was diluted with water and extracted with ether (three 300-ml. portions). The ether extracts were washed with water and brine, dried and concentrated, affording 3-(cyclopropylmethyl)-1,2,3,4,5,6,7,10-octahydro-8-methoxy-6(eq),11(ax)-dimethyl-2,6-methano-3-benzazocine (45.4 g.), part (10- and 20-g. portions) of which was converted into the hydrochloride salt using ethereal hydrogen chloride and concurrently hydrolyzed. Three recrystallizations of the combined salt portions from benzene-methanol afforded white fine crystals of 3-(cyclopropylmethyl)-1,2,3,4,5,6,7,8,9,10-decahydro-6,11-cis-dimethyl-8-oxo-2,6-methano-3-benzazocine hydrochloride (about 8.5 g., m.p. 206°–208° C.), the free base of which is the compound of Formula III wherein Q' is cyclopropylmethyl, X is hydrogen, Y is methyl, Z is hydrogen and Z' is methyl.

H. A mixture of 3-(cyclopropylmethyl)-1,2,3,4,5,6,7,8,9,10-decahydro-6,11-cis-dimethyl-8-oxo-2,6-methano-3-benzazocine hydrochloride (the product of part G of this example, 1.0 g.), hydroxylamine hydrochloride (0.24 g.), ethanol (5 ml.) and pyridine (5 ml.) was refluxed (for 3 hr.), diluted with water, basified with sodium bicarbonate and extracted with chloroform. The chloroform extracts were dried and concentrated. Recrystallization of the residue from ethanol afforded 3-(cyclopropylmethyl)-1,2,3,4,5,6,7,8,9,10-decahydro-6,11-cis-dimethyl-2,6-methano-3-benzazocine-8-one oxime, the compound of Formula IV wherein Q' is cyclopropylmethyl, X is hydrogen, Y is methyl, Z is hydrogen and Z' is methyl. On larger scale the product was obtained as off-white crystals (m.p. 190°–193° C.).

I. Acetic anhydride (1.02 g.) was added to a solution of 3-(cyclopropylmethyl)-1,2,3,4,5,6,7,8,9,10-decahydro-6,11-cis-dimethyl-2,6-methano-3-benzazocine-8-oxime (the product of part (H) of this example, 2.2 g.) in acetic acid (20 ml.). Gaseous hydrogen chloride was bubbled through the solution, which was then refluxed (for 1 hr.) and stripped of solvents. Dilute hydrochloric acid (2N) was added to the residue and the mixture was heated on the steam bath (fpr 2 hr.), basified with aqueous ammonia and extracted with chloroform. The chloroform extracts were dried and concentrated. Ethereal hydrogen chloride was added to a solution of the residue in methanol, affording 8-amino-3-(cyclopropylmethyl)-1,2,3,4,5,6-hexahydro-cis-6,11-dimethyl-2,6-methano-3-benzazocine dihydrochloride, the infrared spectrum of which showed that it was identical with the salt product of part (B) of this example.

EXAMPLE 2

A. A solution of 1,2,3,4,5,6-hexahydro-8-methoxy-cis-6,11-dimethyl-2,6-methano-3-benzazocine (described as 2'-methoxy-5,9-dimethyl-6,7-benzomorphan at J. Org. Chem., 25, 986 (1960); 9.25 g.), tetrahydrofuran (130 ml.) and isopropyl alcohol (130 ml.) was added with stirring to liquid ammonia (about 400 ml.) under reflux. Sodium was then added in pieces (about 15) with continued stirring (during ½ hr.). After further stirring and disappearance of the blue color (about 4 hr. more), methanol (40 ml.) was added and the mixture was warmed to room temperature and allowed to stand overnight. The residual colorless, cloudy solution was diluted with water (600 ml.) and extracted with ether (two 400-ml. portions). The ether extracts were washed with saturated salt solution, dried and concentrated, affording 1,2,3,4,5,6,7,10-octahydro-8-methoxy-6(eq),11(ax)-dimethyl-2,6-methano-3-benzazocine (9.3 g.) as a yellow-brown oil.

Concentrated hydrochloric acid (8 ml. was added to a solution of 1,2,3,4,5,6,7,10-octahydro-8-methoxy-6(eq),-11-(ax)-dimethyl-2,6-methano-3-benzazocine (21 g.) in acetone (50 ml.) and the mixture was kept cold (0° C.) for 5 days. The crystalline product was collected in two corps. Each crop was separately recrystallized from acetone-water and the products were combined, affording off-white crystals of 1,2,3,4,5,6,7,8,9,10-decahydro-6,11-cis-dimethyl-2,6-methano-3-benzazocin-8-one hydrochloride (11 g., 198°–201° C.), the free base of which is the compound of Formula III wherein Q' is hydrogen, X is hydrogen, Y is methyl, Z is hydrogen and Z' is methyl.

B. A solution of 1,2,3,4,5,6,7,8,9,10-decahydro-6,11-cis-dimethyl-2,6-methano-3-benzazocine-8-one hydrochloride (the product of part (A) of this example, 2.0 g.), hydroxylamine hydrochloride (0.6 g.), pyridine (10 ml.) and ethanol (20 ml.) was refluxed (for 2 hr.), then concentrated. The product was triturated with isopropyl alcohol and dried, affording off-white crystals of 1,2,3,4,5,6,7,8,9,10-decahydro-6,11-cis-dimethyl-2,6-methano-3-benzazocin-8-one oxime hydrochloride (1.8 g., m.p. 237°–240° C.), the free base of which is the compound of Formula IV wherein Q' is hydrogen, X is hydrogen, Y is methyl, Z is hydrogen and Z' is methyl.

C. Gaseous hydrogen chloride was bubbled through a mixture of 1,2,3,4,5,6,7,8,9,10-decahydro-6,11-cis-dimethyl-2,6-methano-3-benzazocin-8-one oxime hydrochloride (the product of part (B) of this example, 4.0 g.), acetic anhydride (2.0 g.) and acetic acid (15 ml.). The resulting red solution was heated to reflux; the hydrogen chloride stream was stopped; and the solution was refluxed (for 3 hrs.), then concentrated. A solution of the residual red syrup in dilute hydrochloric acid (6N, 50 ml.) was heated on a steam bath (for 1 hr.) and concentrated. Recrystallization of the resulting purple crystals from aqueous alcohol afforded light orchid crystals of 8-amino-1,2,3,4,5,6,-hexahydro-cis-6,11-dimethyl-2,6-methano-3-benzazocine dihydrochloride hydrate (4 g., m.p.> 280° C.), the free base of which is the compound of Formula V wherein Q° is hydrogen, R is hydrogen, R' is hydrogen, X is hydrogen, Y is methyl, Z is hydrogen and Z' is methyl.

D. A mixture of 8-amino-1,2,3,4,5,6-hexahydro-cis-6,11-dimethyl-2,6-methano-3-benzazocine dihydrochloride hydrate (the product of part (C) of this example, 2 g.), cyclopropanecarbonyl chloride (3 g.), saturated sodium bicarbonate solution (20 ml.) and chloroform (30 ml.) was stirred at ice temperature (for 1 hr.) and then at room temperature (for 1 hr.). The chloroform layer was washed with saturated sodium bicarbonate solution and concentrated, affording as a yellow oil N-(3-(cyclopropanecarbonyl)-1,2,3,4,5,6-hexahydro-6-(eq),11(ax)-dimethyl-2,6-methano-3-benzazocin-8-yl)cyclopropanecarboxamide (3.2 g.), the compound of Formula IX wherein Q' is cyclopropanecarbonyl, R is hydrogen, R" is cyclopropanecarbonyl, X is hydrogen, Y is methyl, Z is hydrogen and Z' is methyl.

E. A solution of N-(3-(cyclopropanecarbonyl)-1,2,3,4,5,6-hexahydro-6(eq),11(ax)-dimethyl-2,6-methano-3-benzazocine-8-yl)cyclopropanecarboxamide (the product of part (D) of this example, 3.8 g.) in tetrahydrofuran (30 ml.) was added to a solution of diborane in tetrahydrofuran (1M as $BH_3$, 50 ml.) with cooling at ice temperature, then the mixture was heated under reflux (for 2 hr.) Dilute hydrochloric acid (5N, 100 ml.) was added cautiously and the clear solution was concentrated under reduced pressure. The aqueous residue was washed with ether, basified with sodium hydroxide solution (35%) and extracted with chloroform. The chloroform extracts were dried and concentrated to a red oil (3.2 g.). A similar reduction of N-[3-(cyclopropanecarbonyl)-1,2,3,4,5,6-hexahydro-6(eq),11(ax)-dimethyl-2,6-methano-3-benzazocine-8-yl]cyclopropanecarboxamide (5.8 g.) also afforded a red oil (5 g.) Crystallization of the red oil from isopropyl acetate afforded white crystals of 3-(cyclopropylmethyl)-8-(cyclopropylmethylamino)-1,2,3,4,5,6-hexahydro-cis-6,11-dimethyl-2,6-methano-3-benzazocine hydrochloride (m.p. 229°–232° C), the free base of which is the compound of Formula I wherein Q is cyclopropylmethyl, R is hydrogen, R' is cyclopropylemthyl, X is hydrogen, Y is methyl, Z is hydrogen and Z' is methyl.

EXAMPLE 3

A. Formic acid (10 ml.) was added dropwise with cooling (to 0° C.) to acetic anhydride (20 ml.) and the resulting solution was heated (to 50° C. for ¼ hr.). A solution of 8-amino-3-(cyclopropylmethyl)-1,2,3,4,5,6-hexahydro-cis-6,11-dimethyl-2,6-methano- 3-benzazocine (the free base product of part (B) of Example 1, 6.7 g.) in formic acid (20 ml.) was added dropwise with cooling (to 0° C.). The resulting mixture was refrigerated ovenight and stripped of solvents. The residue was basified with sodium bicarbonate, then with concentrated aqueous ammonia, and extracted with ether. The ether extracts were dried and stripped of ether, affording N-(3-(cyclopropylmethyl)-1,2,3,4,5,6-hexahydro-6(eq), 11(ax)-dimethyl-2,6-methano-3-benzazocin-8yl)-formamide (5 g.), the compound of Formula VIII wherein Q' is cyclopropylmethyl, R is hydrogen, R" is formyl, X is hydrogen, Y is methyl, Z is hydrogen and Z' is methyl.

B. A mixture of N-(3-(cyclopropylmethyl)-1,2,3,4,5,6-hexahydro-6(eq),11(ax)-dimethyl-2,6-methano-3-benzazocin-8-yl)formamide (the product of part (A) of this example, 5 g.) and a solution of diborane in tetrahydrofuran (1M as $BH_3$, 80 ml.) was refluxed (for 3 hr.), acidified with dilute hydrochloric acid (6N) and stripped of tetrahydrofuran. The aqueous residue was washed with ether, basified with sodium hydroxide and extracted with ether. The ether extracts were dried and stripped of ether. Ethereal hydrogen chloride was added to a solution of the product (3.5 g.) in ethanol, affording off-white crystals of 3-(cyclopropylmethyl)-1,2,3,4,5,6-hexahydro-cis-6,11-dimethyl-8-(methylamino)-2,6-methano-3-benzazocine dihydrochloride ethanolate hydrate (m.p. > 250° C.), the free base of which is the compound of Formula I wherein Q is cyclopropylmethyl, R is hydrogen, R' is methyl, X is hydrogen, Y is methyl, Z is hydrogen and Z' is methyl.

EXAMPLE 4

A. A mixture of 8-amino-1,2,3,4,5,6-hexahydro-cis-6,11-dimethyl-2,6-methano-3-benzazocine dihydrochloride hydrate (the product of part (C) of Example 2, 10 g.), acetic anhydride (20 ml.) and pyridine (100 ml.) was heated on a steam bath (for 4 hr.) and stripped of solvents, affording N-(3-acetyl-1,2,3,4,5,6-hexahydro-6(eq),11(ax)-dimethyl-2,6-methano-3-benzazocin-8-yl)acetamide, the compound of Formula IX wherein Q" is acetyl, R is hydrogen, R" is acetyl, X is hydrogen, Y is methyl, Z is hydrogen and Z' is methyl.

B. A mixture of the entire product of part A of this example and dilute hydrochloric acid (2N):ethanol (1:1) was heated on a steam bath (for 2 hr.), stripped of ethanol, cooled, basified with ammonia and extracted with ether. The ether extracts were dried. The product crystallized from the ether solution and was recrystallized from ethyl acetate, affording off-white crystals of 3-acetyl-8 -amino-1,2,3,4,5,6-hexahydro-cis-6,11-dimethyl-2,6-methano-3-benzazocine (m.p. 208°-209° C.), the compound of Formula VI wherein Q" is acetyl, R is hydrogen, R' is hydrogen, X is hydrogen, Y is methyl, Z is hydrogen and Z' is hydrogen.

C. A mixture of 3-acetyl-8-amino-1,2,3,4,5,6-hexahydro-cis-6,11-dimethyl-2,6-methano-3-benzazocine (the product of part (B) of this example, 20 g.), formalin (35-40%, 25 ml.), ethanol (180 ml.) and a catalytic amount of palladium-on-carbon (10%) was hydrogenated on a Parr apparatus (at 55° C.), then filtered. The filtrate was concentrated and the residue was dissolved in ether. The ether solution was dried and stripped of ether, affording as an oil 3-acetyl-1,2,3,4,5,6-hexahydro-6(eq),11(ax)-dimethyl-8-(dimethylamino)-2,6-methano-3-benzazocine (17.7 g.), the compound of Formula VI wherein Q" is acetyl, R is methyl, R' is methyl, X is hydrogen, Y is methyl, Z is hydrogen and Z' is methyl.

D. A mixture of 3-acetyl-1,2,3,4,5,6-hexahydro-6(eq),- 11(ax)-dimethyl-8-(dimethylamino)-2,5-methano-3-benzazocine (the product of part (C) of this example, 17 g.) and concentrated hydrochloric acid (200 ml.) was refluxed (for 30 hr.), then concentrated. A mixture of the residue and water was basified with concentrated aqueous ammonia and extracted with chloroform. The chloroform extracts were dried and concentrated. The picrate salt of the product was recrystallized from aqueous ethanol and freed of picric acid. The oxalate salt of the product was recrystallized three times from absolute ethanol and freed of oxalic acid, affording as an oil 1,2,3,4,5,6 -hexahydro-6(eq),11(ax)-dimethyl-8-(dimethylamino)-2,6-methano-3-benzazocine, the compound of Formula V wherein Q' is hydrogen, R is methyl, R' is methyl, X is hydrogen, Y is methyl, Z is hydrogen and Z' is methyl.

e. cyclopropanecrbonyl chloride (4 ml.) was added dropwise with stirring and cooling to ice temperature to a mixture of 1,2,3,4,5,6-hexahydro-6(eq),11(ax)-dimethyl-8-(dimethylamino)-2,6-methano-3-benzazocine oxalate (the oxalate salt product of part (D) of this example, 3.5 g.), chloroform (100 ml.) and dilute sodium hydroxide solution (1N, 100 ml.). Stirring was continued at room temperature (for 3hr.) and the mixture was basified with sodium hydroxide. The chloroform layer was washed with saturated sodium bicrbonate solution, dried and stripped of chloroform, affording 3-(cyclopropanecarbonyl)-1,2,3,4,5,6-hexahydro-6(eq), 11(ax)-dimethyl-8-dimethylamino)-2,6-methano-3-benzazocine (4g.), the compound of Formula VI wherein Q" is cyclopropanecarbonyl, R is methyl, R' is methyl, X is hydrogen, Y is methyl, Z is hydrogen and Z' is methyl.

F. A soltuion of 3-(cyclopropanecarbonyl)-1,2,3,4,5,6-hexahydro-6(eq),11(ax)-dimetyl-8-(dimethylamino)-2,6-methano-3-benzazocine (the product of part (E) of this example, 4 g.) in tetrahydrofuran (20 ml.) was added dropwise with stirring to a slurry of lithium aluminum hydride (2 g.) in tetrahydrofuran (70 ml.). The mixture was refluxed (for 3 hr.), then cooled. Saturated sodium potassium tartrate solution was added and the tetrahydrofuran layer was decanted and concentrated. A solution of the residue in ether was washed with water, dried and concentrated. Treatment of the residue with hydrogen chloride and two recrystallizations of the product from ethanol afforded as an off-white powder 3-cyclopropylmethyl-8-dimethylamino-cis-6,11-dimethyl-1,2,3,4,5,6-hexahydro-2,6-methano-3-benzazocine dihydrochloride (m.p. 243°-246° C.), the free base of which is the compound of Formula I wherein Q is cyclopropylmetyl, R is methyl, R' is methyl, X is hydrogen, Y is methyl, Z is hydrogen and Z' is methyl.

G. A mixture of 1,2,3,4,5,6-hexahydro-6(eq,11(ax)-dimethyl-8-nitro-2,6-methano-3-benzazocine hydrochloride (the product of part (C) of Example 1, 14.2 g), sodium bicarbonate (9.5 g.), benzyl chloride (5.8 ml.) and N,N-dimethylformamide (90 ml.) was refluxed (for 4 hr.), then filtered, and the filtrate was concentrated. A solution of the residual syrup in ether was filtered and acidified with ethereal hydrogen chloride. Two recrystallizations of the product (18.2 g.) from ethanol afforded as an off-white powder 1,2,3,4,5,6-hexahydro-3-benzyl-6(eq),11(ax)-dimethyl-8-nitro-3-benzazocine hydrochloride (257+-258°

C.), the free base of which is the compound of Formula II wherein Q' is benzyl, X is hydrogen, Y is methyl, Z is hydrogen and Z' is methyl.

H. Reduction of 1,2,3,4,5,6-hexahydro-3-benzyl-6(eq),-11(ax)-dimethyl-8-nitro-3-benzazocine hydrochloride (the product of part (G) of this example) using iron and hydrochloric acid provides 8-amino-3-benzyl-1,2,3,4,5,6-hexahydro-6(eq), 11(ax)-dimethyl-2,6-methano-3-benzazocine, the compound of Formula V wherein Q° is benzyl, R is hydrogen, R' is hydrogen, X is hydrogen, Y is methyl, Z is hydrogen and Z' is methyl.

I. Reductive methylsation of 8-amino-3-benzyl-1,2,3,4,5,6-hexahydro-6(eq),11(ax)-dimethyl-2,6-methano-3-benzazocine (the product of part (H) of this example) using formaldehyde and formic acid provides 3-benzyl-1,2,3,4,5,6-hexahydro-6(eq), 11(ax)-dimethyl-8-(dimethylamino)-2,6-methano-3-benzazocine, the compound of Formula V wherein Q' is benzyl, R is methyl, R' is methyl, X is hydrogen, Y is methyl, Y is methyl, Z is hydrogen and Z' is methyl.

J. Debenzylation of 3-benzyl-1,2,3,4,5,6-hexahydro-6(eq),11(ax)-dimethyl-8-(dimethylamino)-2,6-methano-3-benzazocine (the product of part I of this example) by catalytic hydrogenation using palladium as catalyst provides 1,2,3,4,5,6-hexahydro-6(eq),1-1(ax)-dimethyl-8-(dimethylamino)-2,6-methano-3-benzazocine, which is identical with the product of part D of this example.

K. Acylation of 1,2,3,4,5,6-hexahydro-6-(eq),1-1(ax)-dimethyl-8-(dimethylamino)-2,6-methano-3-benzazocine (the product of part (D) of this example) with cyclopropanecarbonyl chloride provides 3-(cyclopropanecarbonyl)-1,2,3,4,5,6-hexahydro-6-(eq), 11(ax)-dimethyl-8-(dimethylamino)-2,6-methano-3-benzazocine, which is identical with the product of part (E) of this example.

EXAMPLE 5

A. Isobutyryl chloride (8 ml.) was added dropwise to a solution of 8-amino-1,2,3,4,5,6-hexahydro-cis-6,11-dimethyl-2,6-methano-3-benzazocine (the free base of the product of part (C) of Example 2, 4 g.) and chloroform. Saturated sodium bicarbonate solution (50 ml.) was added and the mixture was refluxed (for 2 hr.). The chloroform layer was washed was saturated sodium bicarbonate solution, dried and concentrated, affording as a red oil N-(3-isobutyryl-1,2,3,4,5,6-hexahydro-6-(eq), 11 (ax)-dimethyl-2,6-methano-3-benzazocin-8-yl)isobutyramide, the compound of Formula IX wherein Q'' is isobutyryl, R is hydrogen, R'' is isobutyryl, X is hydrogen, Y is methyl, Z is hydrogen and Z' is methyl.

B. A solution of N-(3-isobutyryl-1,2,3,4,5,6-hexahydro-6(eq),11(ax)-dimethyl-2,6-methano-3-benzazocin-8-yl)isobutyramide (the product of part (A) of this example, 5 g.), dilute hydrochloric acid (6N, 200 ml.) and ethanol (100 ml.) was heated on a steam bath (for 3 hr.), stripped of ethaol, washed with ether, basified with sodium hydroxide and extracted with ether. The ether extracts were dried and concentrated, affording 8-amino- 3-isobutyryl-1,2,3,4,5,6-hexahydro-6(eq), 11(ax)-dimethyl-2,6-methano-3-benzazocine (about 4 g.), the compound of Formula VI wherein Q'' is isobutyryl, R is hydrogen, R' is hydrogen, X is hydrogen, Y is methyl, Z is hydrogen and Z' is methyl.

C. A solution of 8-amino-3-isobutyryl-1,2,3,4,5,6-hexahydro-6(eq),11(ax)-dimethyl-2,6-methano-3-benzazocine (the product of part (B) of this example, 4 g.) in tetrahydrofuran (50 ml.) was added with stirring to a slurry of lithium aluminum hydride (2.5 g.) in tetrahydrofuran (100 ml.). Stirring was continued and the mixture was refluxed (for 3 hr.), then cooled. Saturated sodium potassium bitartrate solution was added and the tetrahydrofuran layer was decanted and concentrated. Ethereal hydrogen chloride was added to a solution of the residue in ethanol. Recrystallization of the resulting solid from ethanol-ether and then from aqueous ethanol containing concentrated hydrochloric acid afforded as an off-white powder 8-amino- 1,2,3,4,5,6-hexahydro-3-isobutyl-cis-6,11-dimethyl-2,6-methano-3-benzazocine dihydrochloride (m.p.> 300° C.), the free base of which is the compound of Formula I wherein Q is isobutyl, R is hydrogen, R' is hydrogen, X is hydrogen, Y is methyl, Z is hydrogen and Z' is methyl.

EXAMPLE 6

A. A mixture of 8-amino-1,2,3,4,5,6-hexahydro-cis-6,11-dimethyl-2,6-methano-3-benzazocine (the free base of the product of part (C) of Example 2, 3g.), chloroform (80 ml.), saturated sodium bicarbonate solution (80 ml.) and propionyl chloride (5 ml.) was stirred at room temperature (for 2 hr.). The chloroform layer was dried and concentrated, affording as a red oil N-(3-propionyl-1,2,3,4,5,6-hexahydro-6-(eq),11(ax)-dimethyl-2,6-methano-3-benzazocin-8-yl)- propionamide (4.2 g.), the compound of Formula IX wherein Q'' is propionyl, R is hydrogen, R'' is propionyl, X is hydrogen, Y is methyl, Z is hydrogen and Z' is methyl.

B. A mixture of the entire product of part (A) of this example, ethanol (50 ml.) and dilute hydrochloric acid (5N, 25 ml.) was heated on a steam bath (for 1 hr.), then diluted with water. The resulting mixture was washed with ether, basified with ammonia and extracted with ether. The ether extracts were washed with brine, dried and concentrated, affording as a red oil 8-amino-1,2,3,4,5,6-hexahydro-6(eq),11(ax)-dimethyl-3-propionyl-2,6-methano-3-benzazocine (3 g.), the compound of Formula VI wherein Q'' is propionyl, R is hydrogen, R' is hydrogen, X is hydrogen, Y is methyl, Z is hydrogen and Z' is methyl.

C. A solution of the entire product of part (B) of this example in tetrahydrofuran was added with stirring to a slurry of lithium aluminum hydride (0.6 g.) in tetrahydrofuran (about 50 ml. in all). The mixture was stirred under reflux (for 1 hr.), then cooled. Saturated potassium sodium tartrate solution was added and the mixture was filtered. The filtrate was concentrated. Treatment of the residual red oil with hydrogen chloride and recrystallization of the product from methanol-ether afforded as an off-white powder 8-amino-cis-6,11-dimethyl-1,2,3,4,5,6-hexahydro-3-propyl-2,6-methano-3-benzazocine dihydrochloride sesquihydrate (m.r. 202°–207° C.), the free base of which is the compound of Formula I wherein Q is propyl, R is hydrogen, R' is hydrogen, X is hydrogen, Y is methyl, Z is hydrogen and Z' is hydrogen.

EXAMPLE 7

A solution of 8-amino-3-(cyclopropylmethyl)-1,2,3,4,5,6-hexahydro-cis-6,11-dimethyl-2,6-methano-3-benzazocine (the free base product of part (B) of Example 1, 4.4 g.), benzaldehyde (3.2 g.) and ethanol (100 ml.) was refluxed (for 2.5 hr.), then cooled. Sodium borohydride (1.0 g.) was added and the resulting solution was stirred at room temperature (for 2 hr.), then concentrated. The residue was diluted with hydrochloric acid (6%), washed with ether, basified with sodium hydroxide and extracted with ether. The ether extracts were washed with brine, dried and concentrated. Treatment of the residual red oil (5.2 g.) with hydrogen chloride and recrystallization of the product from ethanol afforded as a white powder 3-(cyclopropylmethyl)-1,2,3,4,5,6-hexahydro-cis-6,11-dimethyl-8-benzylamino-2,6-methano-3-benzazocine dihydrochloride (m.r. 233°–237°C.), the free base of which is the compound of Formula I wherein Q is cyclopropylmethyl, R is hydrogen, R' is benzyl, X is hydrogen, Y is methyl, Z is hydrogen and Z' is methyl.

EXAMPLE 8

A. A mixture of 1,2,3,4,5,6,7,8,9,10-decahydro-6,11-cis-dimetyl-2,6-methano-3-benzazocin-8-one hydrochloride (the product of part (A) of Example 2, 5.12 g.), allyl bromide (2.42 g), sodium bicarbonate (3.36 g.) and N,N-dimethylformamide (about 50 ml.) was heated (at 140° C.) with stirring under nitrogen (for 1 hr.), then concentrated. The residue was mixed with water, ether and saturated sodium bicarbonate solution. The ether layer was dried, treated with charcoal and concentrated. Addition of ethereal hydrogen chloride to a solution of the residue in ethaol and recrystallization of the product from ethanol-ether afforded 3-allyl-1,2,3,4,5,6,7,8,9,10-decahydro-6(eq),11(ax)-dimethyl-2,6-methano-3-benzazocin-8-one hydrochloride (4 g.), the free base of which is the compound of Formula III wherein Q' is allyl, X is hydrogen, Y is methyl, Z is hydrogen and Z' is methyl.

B. A mixture of 3-allyl-1,2,3,4,5,6,7,8,9,10-decahydro-6-(eq),11(ax)-dimethyl-2,6-methano-3-benzazocin-8-one hydrochloride (the product of part (A) of this example, 1.7 g.), hydroxylamine hydrochloride (0.4 g.) pyridine (about 10 ml.) and ethanol (about 20 ml.) was refluxed (for 2 hr.), then concentrated. Recrystallization of the residue from ethanol afforded 3-allyl-1,2,3,4,5,6,7,8,9,10-decahydro-6-(eq),11(ax)-dimethyl-2,6-methano-3-benzazocin-8-one oxime hydrochloride, the free base of which is the compound of Formula IV wherein Q' is allyl, X is hydrogen, Y is methyl, Z is hydrogen and Z' is methyl.

C. A refluxing mixture of 3-allyl-1,2,3,4,5,6,7,8,9,10-decahydro-6(eq), 11(ax)-dimethyl-2,6-methano-3-benzazocin-8-one oxime hydrochloride (the product of part (B) of this example,2.1 g.), acetic anhydride (0.7 g.) and acetic acid (about 30 ml.) was saturated with gaseous hydrogen chloride. The resulting red solution was stirred under reflux (for 2 hr.) then concentrated. A mixture of the residue and dilute hydrochloride acid (2N, 40 ml.) was heated on a steam bath (for 1 hr.), then concentrated. Crystallization of the residue from ethanol and recrystallization of the product from ethanol afforded as an off-white powder 8-amino-1,2,3,4,5,6-hexahydro-cis-6,11-dimethyl-3-(2-propenyl)-2,6-methano-3-benzazocine dihydrochloride (m.p. >270° C.), the free base of which is the compound of Formula I wherein Q is allyl, R is hydrogen, R' is hydrogen, X is hydrogen, Y is methyl, Z is hydrogen and Z' is methyl.

EXAMPLE 9

A. Acetic anhydride (20 ml.) and pyridine (10 ml.) were added to a slurry of 8-amino-3-(cyclopropylmethyl)-1,2,3,4,5,6-hexahydro-cis-6,11-dimethyl-2,6-methano-3-benzazocine dihydrochloride (the product of part (B) of Example 1, 3 g.) in chloroform (100 ml.) with cooling at ice temperature. The resulting solution was stirred with continued cooling (for 1 hr.), washed with sodium bicarbonate solution, dried and concentrated, affording as a red oil N-(3-(cyclopropylmethyl)-1,2,3,4,5,6-hexahydro-6(eq),11(aX)-dimethyl-2,6-methano-3-benzazocin-8-yl)acetamide, the compound of Formula VIII wherein Q' is cyclopropylmethyl, R is hydrogen, R'' is acetyl, X is hydrogen, Y is methyl, Z is hydrogen and Z' is methyl.

B. Lithium aluminum hydride (0.5 g.) was added to a solution of N-(3-(cyclopropylmethyl)-1,2,3,4,5,6-hexahydro-6(eq),11(ax)-dimethyl-2,6-methano-3-benzazocin-8-yl)acetamide (the product of part (A) of this example, about 3 g.) in tetrahydrofuran (50 ml.). The slurry was refluxed (for 2 then cooled. Saturated sodium potassium tartrate solution was added, the mixture was filtered and the filtrate was concentrated. An ether solution of the residue was washed with water, dried and concentrated. Distillation of the residual red oil afforded as a yellow viscous oil 3-(cyclopropylmethyl)-8-(ethylamino)-1,2,3,4,5,6-hexahydro-cis-6,11-dimethyl-2,6-methano-3-benzazocine (700 mg., b.r. 155°–160° C./0.03 mm.), the compound of Formula I wherein Q is cyclopropylmethyl, R is hydrogen, R' is ethyl, X is hydrogen, Y is methyl, Z is hydrogen and Z' is methyl.

EXAMPLE 10

A. A mixture of 8-amino-3-(cyclopropylmethyl)-1,2,3,4,5,6-hexahydro-cis-6,11-dimethyl-2,6-methano-3-benzazocine dihydrochloride (the product of part (B) of Example 1, 4 g.), propionic anhydride (4 ml.), pyridine (8 ml.) and chloroform (80 ml.) was stirred overnight at room temperature. The resulting solution was washed with sodium bicarbonate solution, dried and concentrated, affording as a yellow oil N-(3-(cyclopropylmethyl)-1,2,3,4,5,6-hexahydro-6(eq),1-1(ax)-dimethyl-2,6-methano-3-benzazocin-8-yl)propionamide (3.8 g.), the compound of Formula VIII wherein Q' is cyclopropylmethyl, R is hydrogen, R'' is propionyl, X is hydrogen, Y is methyl, Z is hydrogen and Z' is methyl.

B. Lithium aluminum hydride (0.75 g.) was added slowly with cooling at ice temperature to a solution of N-(3-(cyclopropylmethyl)-1,2,3,4,5,6-hexahydro-6(eq),11(ax)-dimethyl-2,6-methano-3-benzazocin-8-yl)propionamide (the product of part (A) of this example, 3.8 g.) in tetrahydrofuran (70 ml.) and the resulting mixture was refluxed (for 1 hr.). Saturated sodium potassium tartrate solution was cautiously added, the slurry was filtered and the filtrate was concentrated. Distillation of the residual oil afforded as an amber oil 3-(cyclopropylmethyl)-1,2,3,4,5,6-hexahydro-cis-6,11-dimethyl-8-(propylamino)-2,6-methano-3-benzazocine (2.0 g., b.r. 155°–160° C./0.05 mm.), the compund of Formula I wherein Q is cyclopropylmethyl, R is propyl, X is hydrogen, Y is methyl, Z is hydrogen and Z' is methyl.

EXAMPLE 11

A. A mixture of 8-amino-3-(cyclopropylmethyl)-1,2,3,4,5,6-hexahydro-cis-6,11-dimethyl-2,6-methano-3-benzazocine dihydrochloride (the product of part (B) of Example 1, 4 g.), butyric anhydride (4 ml.), pyridine (5 ml.) and chloroform (80 ml.) was stirred at ice temperature (for 2 hr.). The resulting solution was washed with sodium bicarbonate solution and concentrated, affording as a yellow oil N-(3-cyclopropylmethyl)-1,2,3,4,5,6-hexahydro-6-(eq),11(ax)-dimethyl-2,6-methano-3-benzazocin-8-yl)butyramide (3.5 g.), the compound of Formula VIII wherein Q' is cyclopropylmethyl, R is hydrogen, R' is butyryl, X is hydrogen, Y is methyl, Z is hydrogen and Z' is methyl.

B. Lithium aluminum hydride (0.75 g.) was added cautiously with cooling at ice temperature to a solution of N-(3-(cyclopropylmethyl)-1,2,3,4,5,6-hexahydro-6(eq),11(ax)-dimethyl-2,6-methano-3-benzazocin-8-yl)butyramide (the product of part (A) of this example, 3.5 g.) in tetrahydrofuran (100 ml.) and the resulting mixture was refluxed (for 3 hr.), then cooled. Saturated sodium potassium tartrate solution was added, the slurry was filtered and the filtrate was concentrated. Distillation of the residual oil afforded as an amber viscous liquid 8-(butylamino)-3-(cyclopropylmethyl)-1,2,3,4,5,6-hexahydro-cis-6,11-dimethyl-2,6-methano-3-benzazocine (2.0 g., b.r. 161°–165° C./0.07 mm.), the compound of Formula I wherein Q is cyclopropylmethyl, R is hydrogen, R' is butyl, X is hydrogen, Y is methyl, Z is hydrogen and Z' is methyl.

EXAMPLE 12

A. Benzyl chloride (250 g.) was added dropwise to a solution of 3,4-diethylpyridine (262 g., Beilsteins Handbuch der Organischen Chemie, Vierte Auflage, Julius Springer, Berlin, 1935 p. 253) in isopropyl alcohol (700 ml.). The resulting solution was refluxed (for 2 hr.), then concentrated under water pump vacuum. Benzene (250 ml.) was added to the residue and the solution was concentrated again. The process was repeated with two further portions (250 ml. and 500 ml.) of benzene. The residue began to crystallize. Benzene (2250 ml.) was added, affording a thick slurry of 1-benzyl-3,4-diethylpyridinium chloride.

B. A Grignard reagent prepared from magnesium (85.5 g.), benzyl chloride (407 g.) and ether (3020 ml.) was added to the slurry product of part (A) os this example. Refluxing was maintained by the heat of reaction during the addition and was continued by applied heat after the addition (for 1.5 hr.). The reaction mixture was quenched in ice-water containing ammonium chloride (453 g.) and the quench was basified with aqueous ammonia. The ether layer was washed with water and stripped of ether, affording 1,2-dibenzyl-3,4-diethyl-1,2-dihydropyridine (712 g.).

C. A solution of sodium borohydride (52 g.) in water (260 ml.) was added to a solution of the entire product of part (B) of this example in ethanol (2 l.). The mixture was stirred (for 3.5 hr.) and allowed to stand overnight at room temperature, then filtered. Water and ether were added to the filtrate. The ether layer was washed with water, dried and concentrated. Vacuum distillation of the residue (714 g.) produced two fractions (408.2 g. and 109.5 g.) which appeared to be only partially reduced. Therefore, dry sodium borohydride (42 g.) was added portionwise to a solution of most (515 g.) of the combined two fractions in absolute ethanol (1 l.). The mixture was stirred at room temperature (for 6 hr.), then concentrated. Water and ether were added to the residue. The ether layer was washed with water, dried and concentrated. Since the product still appeared incompletely reduced, dry sodium borohydride (40 g.) was added to a solution of it in N,N-dimethylformamide (1 l.). The mixture was allowed to stand overnight, diluted with water (2 l.) and extracted with ether. The ether extracts were washed with water, dried and concentrated. Vaccum distillation of the residue afforded as a yellow liquid 1,2-dibenzyl-3,4-diethyl-1,2,5,6-tetrahydropyridine (Fraction II: b.r. 148° C./0.2 mm.–170° C./0.1 mm., 203 g.; Fraction III: b.r. 154°–178° C./0.1 mm., mostly at 174° C., 172 g.).

D. A mixture of 1,2-dibenzyl-3,4-diethyl-1,2,5,6-tetrahydropyridine (Fraction III of part (C) of this example), hydrobromic acid (48%, 1350 ml.) and acetic acid (50 ml.) was refluxed (for 22 hr.), then concentrated. The residue was treated with sodium hydroxide (35%) and extracted with benzene with warming and stirring. The benzene extract was washed with water, dried and concentrared. Vacuum distillation of the residue (155 g.) afforded an orange syrup (Fraction I: b.r. 140° C./0.3 mm.–164° C./0.05 mm., 54.5 g., Fraction II: b.r. 150°–184° C./0.05 mm., 72.3 g.). Oxalic acid (25 g.) was added to a solution of Fraction I of the orange syrup in ethanol (250 ml.), affording the oxalate salt (9.4 g., m.p. 213°–215° C.). Oxalic acid (32 g.) was added to a solution of Fraction II of the orange syrup in ethanol (250 ml.), also affording the oxalate salt (24.9 g., m.p. 216°–221.5° C.). A mixture of most (29.9 g.) of the combined oxalate salts, dilute sodium hydroxide (10%, 400 ml.) and toluene was swirled, then filtered. Concentration of the toluene layer afforded the free base as a yellow syrup (22.6 g.). Treatment of the free base with hydrogen chloride afforded the hydrochloride salt as a white solid (23.8 g., m.r. 202°–205° C). Recrystallization of part (2.5 g.) of the hydrochloride salt from ethyl acetate afforded cis-6,11-diethyl-1,2,3,4,5,6-hexahydro-3-benzyl-2,6-methano-3-benzazocine hydrochloride (m.p. 210°–212.5° C.).

E. A mixture of cis-6,11-diethyl-1,2,3,4,5,6-hexahydro-3-benzyl-2,6-methano-3-benzazocine hydrochloride (the hydrochloride salt product of part (D) of this example, 8.9 g.), ethanol (100 ml.) and palladium-on-carbon (10%, 0.4 g.) was hydrogenated with heating (at 50° C.) on a Parr apparatus, then filtered. Concentration of the filtrate and trituration of the residue with ether afforded a white solid (6.0 g., m.r. 204°–211° C.). Recrystallization of part (all but 2.65 g.) of the white solid first from isopropyl alcohol-ether and then from isopropyl alcohol afforded cis-6,11-diethyl-1,2,3,4,5,6-hexahydro-2,6-methano-3-benzazocine hydrochloride (m.r. 208.5°–211° C., about 3 g.). This hydrochloride salt preparation was combined with two (14.5 g. and 15.4 g.) similar preparations. The combined preparations were shaken with aqueous sodium hydroxide and toluene, and the toluene layer was concentrated. Vacuum distillation of the residue afforded the free base in three fractions (Fraction I: b.r. 78°–90° C./0.03 mm., 3.29 g.; Fraction II: b.r. 90°–98° C./0.03 mm., 14.32 g.; Fraction III; b.p. 98° C./0.03 mm., 9.69 g.).

F. Nitric acid (90%, 70 ml.) was added (during 1 hr.) to a solution of cis-6,11-diethyl-1,2,3,4,5,6-hexahydro-2,6-methano-3-benzazocine (the free base product of part (E) of this example, 22.66 g.) in acetic acid (75 ml.) cooled to ice temperature, then the mixture was allowed to stand overnight at room temperature. Ice (200 g.), water (50 ml.) and sodium hydroxide solution (35%, 125 ml.) were added. The resulting oil solidified, affording in two crops a nitrate salt (31.3 g., m.r. 210°–214° C.; 0.8 g., m.r. 225°–230° C.). Part (21.8 g.) of the nitrate salt was shaken with sodium hydroxide solution (35%), water and ether. The ether layer was washed with water, dried and concentrated. Ethereal hydrogen chloride was added to a solution of the resulting red syrup (16.4 g.) in ethanol (200 ml.). Recrystallization of the resulting first crop (11.0 g., m.r. 285°–286° C.) of crystals from isopropyl alcohol afforded in two crops cis-6,11-diethyl-1,2,3,4,5,6-hexahydro-8-nitro-2,6-methano-3-benzazocine hydrochloride (1.7 g., m.r. 293°–294° C; 7.1 g., m.r. 288°–289° C.), the free base of which is the compound of Formula II wherein Q' is hydrogen, X is hydrogen, Y is ethyl, Z is hydrogen and Z' is ethyl.

G. A mixture of cis-6,11-diethyl-1,2,3,4,5,6-hexahydro-8-nitro-2,6-methano-3-benzazocine hydrochloride (the product of part (F) of this example, 3.11 g.), sodium bicarbonate (2.0 g.), N,N-dimethylformamide (25 ml.) and cyclopropylmethyl bromide (1.60 g.) was refluxed (for 1.5 hr.), then filtered. The solid washed with ethanol and the filtrate was concentrated. The residue was shaken with water and ether. The ether layer was washed with water, treated with charcoal and concentrated. Ethereal hydrogen chloride was added to a solution of the residue (3.0 g.) in ethanol (15 ml.), affording crystalline 3-(cyclopyropylmethyl)-6-(eq),1-1(ax)-diethyl-1,2,3,4,5,6-hexahydro-8-nitro-2,6-methano-3-benzazocine hydrochloride (2.4 g., m.r. 243°–245° C.), the free base of which is the compound of Formula II wherein Q' is cyclopropylmethyl, X is hydrogen, Y is ethyl, Z is hydrogen and Z' is ethyl.

H. A mixture of 3-(cyclopropylmethyl)-6-(eq),1-1(ax)-diethyl-1,2,3,4,5,6-hexahydro-8-nitro-2,6-methano-3-benzazocine hydrochloride (the product of part (G) of this example, 2.4 g.), water (6 ml.), ethanol (11 ml.), iron filings (2.3 g.) and concentrated hydrochloric acid (2 drops) was heated on a steam bath with stirring (for 7 hr.). Sodium bicarbonate (1.5 g.) was added and the mixture was filtered. The solid was washed with ethanol and the filtrate was concentrated. The residue was partitioned between water and chloroform and the chloroform layer was concentrated. trituration of the resulting syrup (3.6 g.) with ether afforded a yellow powder. Addition of ethereal hydrogen chloride to a solution of the yellow powder in ethanol afforded crystals in two crops (0.9 g., m.p. 237° C.; 0.9 g., m.r. 226°–234° C.). Combination and recyrstallization of the two crops from aqueous acetone afforded also in two crops white crystals of 8-amino-3-(cyclopropylmethyl)-cis-6,11-diethyl-1,2,3,4,5,6-hexahydro-2,6-methano-3-benzazocine dihydrochloride (m.r. 290°–292° C. and m.r. 287°–290° C., total of 1.04 g.), the free base of which is the compound of Formula I wherein Q is cyclopropylmethyl, X is hydrogen, Y is ethyl, Z is hydrogen and Z' is ethyl.

As stated above the compounds of Formula I are useful as strong analgesics, which can be demonstrated by standard pharmacological procedures readily carried out by technicians having ordinary skill in pharmacological test procedures. Thus, the test results for a particular compond can be determined without extensive experimentation.

All of the compounds of Formula I of the examples were tested and determined to be active in the acetylcholine writhing test, a primary screening test for analgesia. In this test the ability of test compounds to prevent acetylcholine-induced writhing in mice is determined. The following is an adaptation of the method of Collier and co-workers (Brit. J. Pharmacol. Chemother., 32, 295(1968)) by Anne K. Pierson. An intraperitoneal injection of acetyl-choline (3.2 mg/kg.) causes mice to exhibit writhing, which is a abdominal constriction, and sometimes twisting, followed by extension of the hind limbs. The mice are dosed with the test compound plus vehicle or vehicle alone (controls) 20 minutes prior to, and are observed for 2 minutes after, the acetylchloine injection. During the 2-minute observation period mice not responding by writhing are scored protected and mice responding by writhing one or more times are scored not protected. The mice are dosed orally (usually at 150–200 mg./kg.) or subcutaneously (usually at 75–100 mg./kg.). Fifteen mice per does level are used. Ed$_{50}$ values for active compounds are calculated by probit analysis (C. I. Bliss, The Statistics of Bioassay, Academic Press, New York, 1952) of quantal scores of tests at four or more appropriate dose levels. The following subcutaneous ED$_{50}$ values for the compounds of Formula I of the examples were determined.

| Compound of | ED$_{50}$ Value (mg./kg.) |
|---|---|
| Example 1B | 0.80 |
| Example 2E | 0.70 |
| Example 3B | 0.44 |
| Example 4F | 0.79 |
| Example 5C | 1.5 |
| Example 6C | 5.6 |
| Example 7 | 1.6 |
| Example 8C | 2.5 |
| Example 9B | 1.3 |
| Example 10B | 1.2 |
| Example 11B | 1.0 |
| Example 12H | 1.3 |

We claim:

1. 1,2,3,4,5,6-Hexahydro-3-Q'-8RR''N-5-X-6-Y-11-Z-11-Z'-2,6-methano-3-benzazocine having the formula

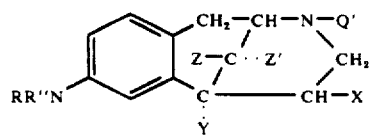

wherein:

Q' is hydrogen, benzyl, propyl, isobutyl, neopentyl, allyl, 2-methyl-2-propenyl, 2-chloro-2-propenyl, cis-3-chloro-2-propenyl, cis-3-chloro-2-butenyl, trans-3-chloro-2-butenyl, propargyl, cyclopropylmethyl or (2,2-dichlorocyclopropyl)methyl;

R is hydrogen or methyl;

R'' is formyl, acetyl, propionyl, butyryl, isobutyryl, benzoyl or cyclopropanecarbonyl;

X is hydrogen, methyl or ethyl;

Y is hydrogen, methyl, ethyl, propyl, allyl or phenyl;

Z is hydrogen, methyl, ethyl or hydroxy; and

Z' is hydrogen, methyl or ethyl;

or an acid addition salt thereof.

2. A compound according to claim 1 wherein X is hydrogen and Z is hydrogen or an acid addition salt thereof.

3. A compound according to claim 2 wherein Y is methyl and Z' is methyl or an acid addition salt thereof.

4. A compound according to claim 3 wherein R is hydrogen or an acid addition salt thereof.

5. A compound according to claim 4 wherein Q' is cyclopropylmethyl or an acid addition salt thereof.

6. A compound according to claim 5 wherein R" is formyl or an acid addition salt thereof.

7. A compound according to claim 5 wherein R" is acetyl or an acid addition salt thereof.

8. A compound according to claim 5 wherein R" is propionyl or an acid addition salt thereof.

9. A compound according to claim 5 wherein R" is butyryl or an acid addition salt thereof.

10. 1,2,3,4,5,6-Hexahydro-3-Q"-8RR"N-5X-6-Y-11-Z-11Z'-2,6-methano-3-benzazocine having the formula

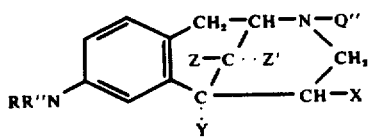

wherein:
Q" is formyl, acetyl or Q* wherein Q* is propionyl, isobutyryl, pivaloyl, acryloyl, 2-methylacryloyl, 2-chloroacryloyl, cis-3-chloroacryloyl, cis-3-chlorocrotonoyl, trans-3-chlorocrotonoyl, propiolyl, cyclopropanecarbonyl or 2,2-dichlorocyclopropanecarbonyl;

R is hydrogen or methyl;
R" is formyl, acetyl, propionyl, butyryl, isobutyryl, benzoyl or cyclopropanecarbonyl;
X is hydrogen, methyl or ethyl;
Y is hydrogen, methyl, ethyl, propyl, allyl or phenyl;
Z is hydrogen, methyl, ethyl or hydroxy; and
Z' is hydrogen, methyl or ethyl.

11. A compound according to claim 10 wherein X is hydrogen and Z is hydrogen.

12. A compound according to claim 11 wherin Y is methyl and Z' is methyl.

13. A compound according to claim 12 wherein R is hydrogen.

14. A compound according to claim 13 wherein Q" is cyclopropanecarbonyl.

15. A compound according to claim 14 wherein R" is cyclopropanecarbonyl.

16. A compound according to claim 13 wherein Q" is acetyl.

17. A compound according to claim 16 wherein R" is acetyl.

18. A compound according to claim 13 wherein Q" is isobutyryl.

19. A compound according to claim 18 wherein R" is isobutyryl.

20. A compound according to claim 13 wherein Q" is propionyl.

21. A compound according to claim 20 wherein R" is propionyl.

* * * * *